US012447279B2

(12) United States Patent
Jugl et al.

(10) Patent No.: US 12,447,279 B2
(45) Date of Patent: Oct. 21, 2025

(54) DRUG DELIVERY DEVICE AND METHOD FOR DETERMINING A DOSE

(71) Applicant: Sanofi, Paris (FR)

(72) Inventors: Michael Jugl, Frankfurt am Main (DE); Stefan Blancke, Frankfurt am Main (DE)

(73) Assignee: Sanofi, Paris (FR)

( * ) Notice: Subject to any disclaimer, the term of this patent is extended or adjusted under 35 U.S.C. 154(b) by 380 days.

(21) Appl. No.: 17/928,107

(22) PCT Filed: Jun. 8, 2021

(86) PCT No.: PCT/EP2021/065202
§ 371 (c)(1),
(2) Date: Nov. 28, 2022

(87) PCT Pub. No.: WO2021/249962
PCT Pub. Date: Dec. 16, 2021

(65) Prior Publication Data

US 2023/0293822 A1 Sep. 21, 2023

(30) Foreign Application Priority Data

Jun. 9, 2020 (EP) .................................... 20315298

(51) Int. Cl.
*A61M 5/315* (2006.01)

(52) U.S. Cl.
CPC ..... *A61M 5/31551* (2013.01); *A61M 2205/50* (2013.01); *A61M 2205/587* (2013.01)

(58) Field of Classification Search
CPC .......... A61M 5/31551; A61M 2205/50; A61M 2205/587; A61M 2205/3306; A61M 5/2422
See application file for complete search history.

(56) References Cited

U.S. PATENT DOCUMENTS 6,277,099 B1 8/2001 Strowe et al.
2010/0331806 A1* 12/2010 Plumptre .......... A61M 5/31585 604/207

(Continued)

FOREIGN PATENT DOCUMENTS

EP 2767297 8/2014
EP 3184137 6/2017

(Continued)

OTHER PUBLICATIONS

International Preliminary Report on Patentability in International Appln. No. PCT/EP2021/065202, mailed on Dec. 22, 2022, 13 pages.

(Continued)

*Primary Examiner* — Donnell A Long
(74) *Attorney, Agent, or Firm* — Bond, Schoeneck & King, PLLC

(57) ABSTRACT

The present disclosure refers to a drug delivery device including, a dose setting and/or drive mechanism including a stationary housing having at least one internal groove on an inner surface; a driver positioned within the housing which is moveable relative to the housing during dose dialing and which is moveable relative to the housing during dose dispensing; and at least one flexible tab that is biased to engage the at least one internal groove such that the at least one flexible tab repeatedly engages and disengages the at least one internal groove during dose dialing or during dose dispensing, thereby performing an oscillating movement between two positions including a first position in which the at least one flexible tab engages the at least one internal groove and a second position in which the at least one flexible tab is disengaged from the at least one internal groove.

20 Claims, 3 Drawing Sheets

(56) References Cited

U.S. PATENT DOCUMENTS

| | | | | |
|---|---|---|---|---|
| 2016/0378951 | A1 | 12/2016 | Gofman et al. | |
| 2019/0269859 | A1 | 9/2019 | Jacobsen | |
| 2021/0369946 | A1 * | 12/2021 | Akerele-Ale ....... | A61M 5/2466 |

FOREIGN PATENT DOCUMENTS

| | | | |
|---|---|---|---|
| EP | 2926846 | | 7/2018 |
| EP | 2911717 | | 5/2019 |
| EP | 2890434 | | 4/2020 |
| JP | 2001087386 | A | 4/2001 |
| JP | 2019532745 | A | 11/2019 |
| WO | WO 2010/139636 | | 12/2010 |
| WO | 2018078178 | A1 | 5/2018 |
| WO | 2019149918 | A1 | 8/2019 |
| WO | WO 2021/249962 | | 12/2021 |

OTHER PUBLICATIONS

International Search Report and Written Opinion in International Appln. No. PCT/EP2021/065202, mailed on Sep. 8, 2021, 15 pages.
Decision to Grant a Patent, JP Patent Application No. 2022-575719, dated Apr. 8, 2025, pp. 1-5 (with pp. 1-2 being a translation).
Notice of Reasons for Rejection, JP Patent Application No. 2022-575719, dated Oct. 8, 2024, pp. 1-19 (with pp. 1-9 being a translation).

* cited by examiner

DRUG DELIVERY DEVICE AND METHOD FOR DETERMINING A DOSE

CROSS REFERENCE TO RELATED APPLICATIONS

The present application is the national stage entry of International Patent Application No. PCT/EP2021/065202, filed on Jun. 8, 2021, and claims priority to Application No. EP 20315298.8, filed on Jun. 9, 2020, the disclosures of which are incorporated herein by reference.

TECHNICAL FIELD

The present disclosure is generally directed to a drug delivery device. Further, the present disclosure is directed to a method for determining a dialed or dispensed dose of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is generally applicable for disposable and reusable devices. However, the present disclosure is especially applicable in pre-filled, disposable pen type devices.

Such drug delivery devices typically include dose setting and/or a drive mechanism to select an individual dose and to deliver this dose by displacing the piston in a cartridge containing a medicament.

It is important for patients to be able to precisely select (dial) a desired dose prior to dispensing, thereby avoiding underdosage or overdosage which may result in severe health problems. For this purpose, it is known to provide a display on which the actually selected dose is indicated. In addition, a tactile or audible feedback may be generated, for example a click sound for each dose unit dialed. WO 2010/139636 A1 and EP 2 890 434 B1 each disclose such a drug delivery device having a display and a feedback mechanism including a detent or clicker which provides the user with an audible and tactile feedback as a dose is set. This known feedback mechanism includes a flexible tab which overrides a grooves as a driver is rotated during dose dialing.

In addition to providing a feedback or indication relating to the currently selected dose to the patient, it is known to track and manage data relating to the type and/or amount of drug administered. For example, EP 2 926 846 B1 proposes a system including an RFID reader to identify the type of drug contained in a cartridge. Further, this system includes an accelerometer to detect movement of the device. Similar systems are known from EP 2 911 717 B1 and EP 2 767 297 A2.

SUMMARY

It is an aspect of the present disclosure to provide an improved drug delivery device allowing reliable and cost-effective detection of the selected dose. It is a further aspect to provide a method for determining the selected dose.

One aspect of the disclosure relates to a drug delivery device including, a cartridge holder which is configured to contain a cartridge and is connected to a dose dialing and/or dispensing assembly. The dose dialing and/or dispensing assembly may include an outer housing and an inner stationary housing having at least one internal groove on an inner surface. The dose dialing and/or dispensing assembly may further include a driver positioned within the inner housing which is moveable, e.g., rotatable, relative to the inner housing during dose dialing and which is moveable, e.g., axially displaceable, relative to the inner housing during dose dispensing. In other words, the driver is preverably moveable during both dose setting and dose delivery. Preferably, the driver is rotationally constrained to the inner housing during dose dispensing. The drug delivery device includes at least one flexible tab that may be biased to engage the at least one internal groove such that the at least one flexible tab repeatedly engages and disengages the at least one internal groove during dose dialing or during dose dispensing. In other words, the at least one flexible tab may perform an oscillating movement between two positions, namely a first position in which the at least one flexible tab engages the at least one internal groove and a second position in which the at least one flexible tab is disengaged from the at least one internal groove. For example, the drug delivery device may have a configuration as the devices disclosed in WO 2010/139636 A1 or in EP 2 890 434 B1. Preferably, the at least one flexible tab is biased into engagement with the at least one groove and may be deflected under elastic deformation when disengaging from the groove, i.e., overriding the groove. In other words, the term 'flexible' expresses the fact that the tab according to the present disclosure is preferably capable of bending easily without breaking, i.e., of bending elastically. Preferably, the oscillating movement of the at least one flexible tab is a radial movement, i.e., substantially perpendicular to the longitudinal axis of the device.

According to one aspect of the disclosure, the drug delivery device includes at least one micro-electro-mechanical system (in the following: MEMS) with at least one sensor configured and arranged to detect the oscillating movement of the at least one flexible tab during dose dialing or during dose dispensing. Detecting the dialing or dispensing based on movements of a clicker may be used for the calculation of the injected and/or dialed doses. The use of a MEMS sensor permits application even under very limited space conditions. The costs for implementing a MEMS sensor are relatively low, allowing the use of such a MEMS sensor even in disposable drug delivery devices. Yet, a MEMS sensor detects movements in a highly reliable and reproducible manner such that its application meets the high standards for medical devices, such as drug delivery devices.

One embodiment of the present disclosure includes an acceleration sensor, i.e., an accelerometer, located on the at least one flexible tab. Thus, it is possible to detect movement of the flexible tab directly on the tab itself. Accelerometers consisting of a cantilever beam with proof mass are among the smallest MEMS sensors. Such accelerometers are available as two-dimensional and three-dimensional forms to measure velocity along with orientation. As an alternative, a piezoelectric accelerometer or an accelerometer including a mass and a spring may be used as a MEMS sensor for detecting the oscillating movement of the at least one flexible tab during dose dialing.

In an alternative embodiment, an optical sensor may be used as a MEMS sensor to detect the oscillating movement of the at least one flexible tab during dose dialing. In this embodiment, the drug delivery device may further include a light source emitting light which may be detected by the optical sensor. The oscillating movement of the at least one flexible tab may be used to align or misalign the light emitted from the light source and the optical detector.

For example, the at least one optical sensor may be located on the at least one flexible tab and aligned to the light source such that light emitted by the light source can be detected by the sensor only in one of the first or second position, whereas light emitted by the light source can not be detected by the sensor in the other of the two positions.

In an alternative example, the light source may be located on the at least one flexible tab, wherein the at least one optical sensor is located aligned to the light source such that light emitted by the light source can be detected by the sensor only in one of the first or second position, whereas light emitted by the light source can not be detected by the sensor in the other of the two positions.

In still another example, the at least one flexible tab may be made of a light transmitting material and the light source may be located to introduce light into the at least one flexible tab. The at least one optical sensor may be located aligned to the at least one flexible tab such that light emitted by the at least one flexible tab can be detected by the sensor only in one of the first or second position, whereas light emitted by the light source can not be detected by the sensor in the other of the two positions.

According to a further aspect of the present disclosure, the at least one MEMS further includes a microprocessor which is operatively connected to the at least one sensor, to a power source and to a memory. Preferably, the microprocessor is configured to determine a dose amount selected by rotation of the driver during dose dialing. Determination of a dose amount may be based on an even distribution of the grooves corresponding to a certain amount of dose, e.g., a certain number of dose units. As an alternative, an uneven distribution of the grooves may be chosen, e.g., if it is intended to further detect the direction of rotation.

The signals detected by the at least one MEMS may be processed and/or stored in the drug delivery device and/or on a remote device. For example, the drug delivery device may further include a communication unit connected to the at least one MEMS and configured to transmit data corresponding to the dose amount determined by the microprocessor to a remote data management unit, e.g., a glucose meter, a mobile phone, a personal computer, or a network server.

In the drug delivery device, the groove may be parallel to the longitudinal axis of the inner housing. As an alternative, the groove may be helical along the axis of the inner housing. The groove can be parallel to the axis of the inner housing or it can be helical. When the groove is parallel, the driver will not rotate during dose injection and when the groove is helical, the driver will rotate following the path of the groove during dose injection thus defining a transmission ratio.

Preferably, the drug delivery device further includes a blocking member slidably positioned inside the driver that locks the flexible tab into the groove during dose dispensing such that the driver follows the path of the groove. In other words, the drug delivery device may switch between a dose dialing mode in which rotation of the driver is permitted and a dose dispensing mode in which rotation of the driver is prevented due to the engagement with the blocking member.

In one embodiment, the at least one flexible tab may be an integral part of the driver. For example, the blocking member may be provided with an aperture or pocket that is aligned with the flexible tab when the blocking member is in a non-locked position, i.e., in the dose dialing mode, and is misaligned with the flexible tab when in the locked position, i.e., in the dose dispensing mode.

According to one aspect of the present disclosure, the at least one flexible tab may be an, e.g., integral, part of the driver and may have an orientation directed or inclined radially outwards such that the tab may engage at least one internal groove on an inner surface of a stationary housing. In other words, the driver may be located radially inside the stationary housing with the at least one flexible tab of the driver engaging and disengaging the, preferably helical, groove of the stationary housing during the, e.g., oscillating, movement.

In an alternative embodiment, the locking member is provided with the at least one flexible tab. For example, the driver may have an aperture or pocket that is aligned with the flexible tab when the blocking member is in a non-locked position, i.e., in the dose dialing mode, and is misaligned with the flexible tab when in the locked position, i.e., in the dose dispensing mode.

The drug delivery device may include a feedback mechanism generating an audible and/or tactile feedback to a user, e.g. during dose dialing and/or during dose dispensing. For example, the oscillating movement of the at least one flexible tab between the first position and the second position may generate a tactile and/or audile feedback to the user. In addition or as an alternative, the drug delivery device may include a dose display, e.g. including a number sleeve.

The present disclosure is applicable for devices which are manually driven, e.g., by a user applying a force to an injection button, for devices which are driven by a spring or the like and for devices which combine these two concepts, i.e., spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

The present disclosure is further directed to a method for determining a dialed dose in a drug delivery device, especially in a drug delivery device as defined above. Thus, the drug delivery device may include a stationary housing having at least one internal groove on an inner surface; a driver positioned within the housing which is rotatable relative to the housing during dose dialing and which is axially displaceable relative to the housing during dose dispensing; at least one flexible tab that is biased to engage the at least one internal groove such that the at least one flexible tab repeatedly engages and disengages the at least one internal groove during dose dialing, thereby performing an oscillating movement between two positions including a first position in which the at least one flexible tab engages the at least one internal groove and a second position in which the at least one flexible tab is disengaged from the at least one internal groove; and at least one MEMS including at least one sensor configured and arranged to detect the oscillating movement of the at least one flexible tab during dose dialing, a microprocessor which is operatively connected to the at least one sensor, to a power source and to a memory, wherein the microprocessor is configured to determine a dose amount selected by rotation of the driver during dose dialing. The method includes the steps of dialing a dose by rotating the driver and, preferably at the same time, inducing the at least one sensor of the at least one MEMS to detect the oscillating movement of the at least one flexible tab and processing a signal generated by the at least one sensor in response to the oscillating movement of the at least one flexible tab in the microprocessor to determine a dose amount selected by rotation of the driver during dose dialing. The MEMS sensor may be induced to detect the movement of the at least one tab by switching on or waking up the MEMS and/or the microprocessor. This may be effected via a trigger or switch which may be operated by a user or which may be operated automatically upon actuation of the drug delivery device or its components. In a further alternative, a movement of the drug delivery device ora change in its status, e.g., removal of a cap, may be used to switch on or wake up the MEMS and/or the microprocessor. Preferably, the microprocessor is configured to determine a dose amount selected by rotation of the driver during dose dialing based on counting the signals received from the MEMS sensor. For example, with an even distribution of the grooves, each signal corresponds to a certain amount of dose or dose increment, i.e., a certain number of dose units. As an alternative, an uneven distribution of the grooves may be chosen, e.g., if it is intended to further detect the direction of rotation.

In an exemplary embodiment of the present disclosure, a drug delivery device may include: a dose setting and/or drive mechanism including a stationary housing having at least one internal groove, e.g., at least one helical groove, on an inner surface;

a driver positioned within the stationary housing which is moveable relative to the stationary housing both during dose setting and during dose delivery, e.g., rotatable relative to the housing during dose dialing and axially displaceable relative to the housing during dose dispensing; at least one flexible tab provided as an integral part of the driver and biased to engage the at least one internal groove of the stationary housing such that the at least one flexible tab repeatedly engages and disengages the at least one internal groove during dose dialing or during dose dispensing, preferably by elastically bending radially outwards, thereby performing an oscillating movement between two positions including a first position in which the at least one flexible tab engages the at least one internal groove and a second position in which the at least one flexible tab is disengaged from the at least one internal groove; and at least one micro-electro-mechanical system including at least one sensor configured and arranged to detect the oscillating movement of the at least one flexible tab during dose dialing or during dose dispensing.

While the present disclosure is explained with reference to an element moving during dose dialing, the present disclosure further refers to detecting movement of a component part during dose dispensing, thereby permitting determining the amount of dose dispensed instead of the amount of dose selected (dialed).

The drug delivery device may include a cartridge containing a medicament. The terms “drug” or “medicament” are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient (“API”), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or “drug container” adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

BRIEF DESCRIPTION OF THE FIGURES

Non-limiting, exemplary embodiments of the invention will now be described with reference to the accompanying drawings, in which.

DETAILED DESCRIPTION

Figure 1:
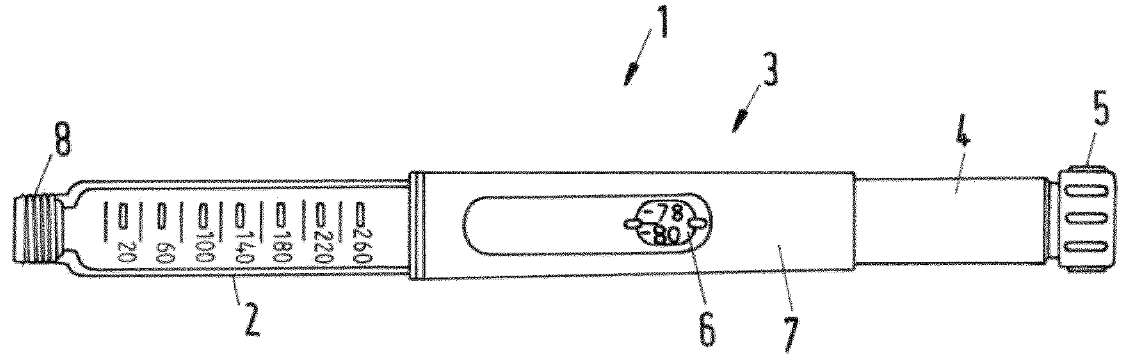
FIG. 1 is a view of a resettable drug delivery device.

In the Figures, identical elements, identically acting elements or elements of the same kind may be provided with the same reference numerals.

The terms "axial", "radial", or "circumferential" as used herein may be used with respect to a main longitudinal axis of the device, the cartridge, the housing or the cartridge holder, e.g., the axis which extends through the proximal and distal ends of the cartridge, the cartridge holder or the drug delivery device.

"Distal" is used herein to specify directions, ends or surfaces which are arranged or are to be arranged to face or point towards a dispensing end of the drug delivery device, i.e., the left side in FIG. 1, or components thereof and/or point away from, are to be arranged to face away from or face away from the proximal end, i.e., the right side in FIG. 1. On the other hand, "proximal" is used to specify directions, ends or surfaces which are arranged or are to be arranged to face away from or point away from the dispensing end and/or from the distal end of the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example.

In general, the drug delivery device may have substantially the configuration and functions as disclosed in WO 2010/139636 A1 or in EP 2 890 434 B1 to which reference is made regarding the description of the component parts and their functions.

Referring to FIG. 1, there is shown a drug delivery device 1 in accordance with an exemplary arrangement. The drug delivery device 1 includes a first cartridge retaining part 2, and a dose setting and/or drive mechanism 3 including. A number (or dose dialing) sleeve 4 of the dose setting and/or drive mechanism 3 is rotatable by actuation of a dose dial grip 5. The device further includes a dose display 6 which may include a lens or window permitting view on a portion of the number (or dose dialing) sleeve 4, which is partially received in an outer housing 7.

The drug delivery device may be a resettable drug delivery device (i.e., a reusable device) or alternatively a non-resettable drug delivery device (i.e., a non-reusable device). The cartridge retaining part 2 and the dose setting and/or drive mechanism 3 are secured together by connecting features. For non-resettable devices, these connecting features would be permanent and non-reversible. For resettable devices, these connecting features would be releasable. In this illustrated arrangement, the cartridge housing 2 is secured within the housing 5 of the dose setting and/or drive mechanism 3. A removable cap (not shown) may be releasably retained over a distal end of a cartridge retaining part 2 or cartridge housing. Preferably, the distal end of the cartridge retaining part 2 or cartridge housing includes a hub 8 for attaching a removable needle assembly (not shown).

The dose setting and/or drive mechanism 3 further includes an inner housing 9 which is secured to the outer housing 7 to be stationary. The inner housing 9 is provided with at least one groove 10 on its inner surface. In the embodiment depicted in FIG. 2, several grooves 10 are shown extending axially, i.e., in the direction from the distal end of the drug delivery device 1 to its proximal end. In the alternative embodiment depicted in FIG. 3 several grooves 10 are shown extending helically. Further, the inner housing 9 may be provided with an external thread as shown in FIGS. 2 and 3, e.g. for engaging the number (or dose dialing) sleeve 4.

Figure 2:
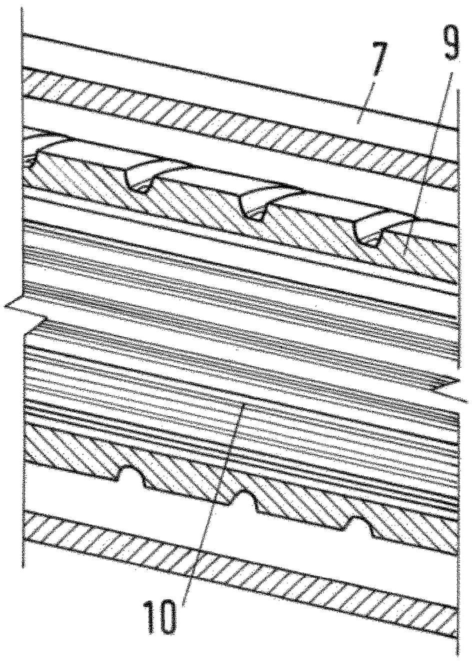
FIG. 2 is a cross sectional view of a portion of the device of FIG. 1 according to a first embodiment.
Figure 3:
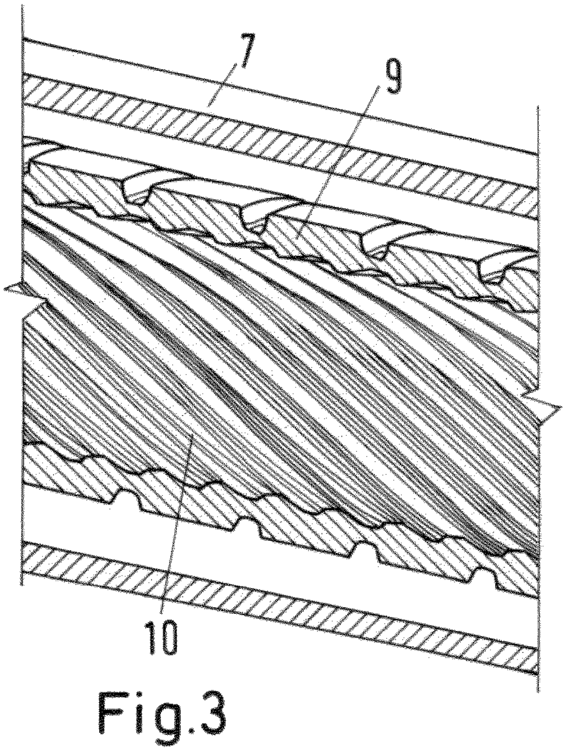
FIG. 3 is a cross sectional view of a portion of the device of FIG. 1 according to a second embodiment.
Figure 4:
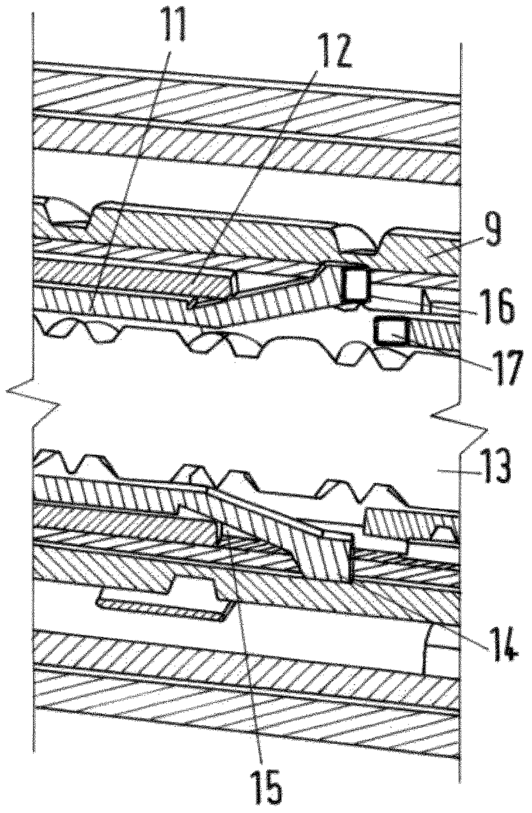
FIG. 4 is a close-up of the cross sectional view of a third embodiment showing a locking member in an un-locked position.
Figure 5:
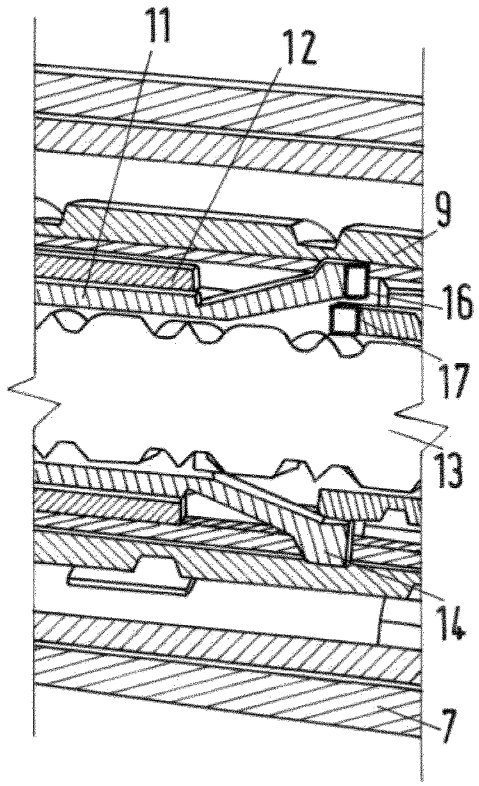
FIG. 5 is a close-up of the cross sectional view of the third embodiment showing the locking member in a locked position.

FIGS. 4 and 5 depict a further embodiment wherein the inner housing 9 has axially extending grooves 10 as in FIG. 2. In this embodiment, a driver 11, a clutch sleeve 12 and a piston rod 13 of the dose setting and/or drive mechanism 3 are provided in a similar manner as disclosed in disclosed in WO 2010/139636 A1. In other words, the piston rod 13 is received in the driver 11, the driver 11 is a received in the clutch sleeve 12 and the clutch sleeve 12 is received in the inner housing 9.

As can be seen in FIGS. 4 and 5, the driver includes several flexible tabs 14 engaging with their free ends the respective grooves 10 of the inner housing 9. The clutch sleeve 12 is provided with apertures 15 permitting the flexible tabs 14 to pass through the clutch sleeve 12 for interaction with the grooves 10 of the inner housing 9. The flexible tabs 14 made disengage from the grooves 10 and may be flexed radially inwards against the spring force exerted by the flexible tabs 14.

Comparing FIGS. 4 and 5 it is evident that the clutch sleeve 12 and the driver 11 may be displaced relative to each other in the axial direction. The relative position depicted in FIG. 4 is a dose dialing position in which the driver 11 and the clutch sleeve 12 may be rotated together with the number (or dose dialing) sleeve 4 and the dose dial grip 5 relative to the outer housing 7 and the inner housing 9 to select a dose. Due to this rotation, the flexible tabs 14 are repeatedly forced out of engagement with the respective grooves 10 and the flexible back into engagement with the next groove 10. In other words, the flexible tabs 14 may override of the grooves 10 during dose dialing. This may generate an audible and/or tactile feedback. This oscillating movement of the flexible tabs 14 is indicative of dose dialing.

The relative position depicted in FIG. 5 is a dose dispensing position in which the driver 11 and to the clutch sleeve 12 are displaced relative to each other compared with the dose dialing position of FIG. 4. This made disengage a rotational clutch between the clutch sleeve 12 and the number (or dose dialing) sleeve 4. In the dose dispensing position, the driver 11 and the clutch sleeve 12 may be displaced axially, preferably without rotation, relative to the outer housing 7 and the inner housing 9. This axial displacement may be caused by a user pressing on dose dial grip 5 which causes the number (or dose dialing) sleeve 4 to rotate back into the outer housing 7 as disclosed in disclosed in WO 2010/139636 A1. Due to the axial displacement between the driver 11 and the clutch sleeve 12, the respective free ends of the flexible tabs 14 are displaced relative to the apertures 15, too, thereby preventing that the flexible tabs 14 are allowed to disengage from the respective grooves 10. Thus, the clutch sleeve 12 acts as a blocking member preventing disengagement of the flexible tabs 14 from the grooves 10 in the dose dispensing position of the drug delivery device.

In the embodiment depicted in FIGS. 4 and 5, the free end of one of the flexible tabs 14 is provided with an optical sensor 16, e.g. a MEMS sensor. Further, a light source 17, e.g., an LED, is provided in one of the apertures 15. The optical sensor 16 and the light source 17 are aligned to each other such that light emitted by the light source 17 may be detected if the respective flexible tab 14 is flexed radially inwards upon disengagement of the grooves 10. On the other hand, in the positions depicted in FIGS. 4 and 5, i.e., with the flexible tabs 14 engaging the respective grooves 10, the optical sensor 16 and to the light source 17 are located such that the light emitted by the light source 17 can not be detected by the optical sensor 16.

The oscillating movement of the flexible tabs 14 during dose dialing may be detected by the optical sensor 16 as the light emitted from the light source 17 is repeatedly detected and prevented from being detected by the optical sensor 16 as the driver 11 rotates relative to the inner housing 9. The signal generated by the optical sensor 16 may be processed and/or stored in a microprocessor (not shown) connected to the optical sensor 16. The amount of dose selected by rotation of the driver 11 may be determined by the microprocessor on the basis of the signal generated by the optical sensor 16 in response to the oscillating radial movement of the flexible tabs 14 during dose dialing.

In a not shown alternative, the MEMS optical sensor 16 may be provided in or on the clutch sleeve 12 while the light source 17 is provided in or on the flexible tab 14.

Figure 6:
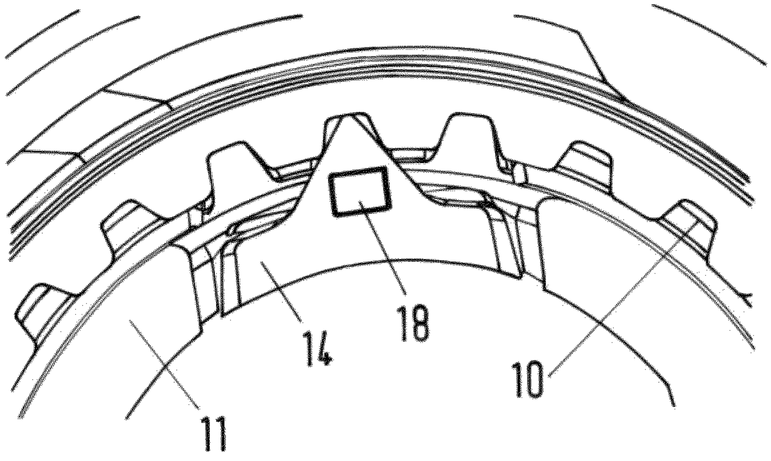
FIG. 6 is a cross sectional view of a fourth embodiment.

A further embodiment is depicted in FIG. 6 showing a sectional view of a drug delivery device including an inner housing 9 with a series of axially extending grooves 10 on its inner surface and a driver 11 with at least one flexible tab 14 engaging the grooves 10. Again, relative rotation between the driver 11 and the inner housing 9 occurs during dose dialing which results in an oscillating radial movement of the flexible tab 14 as it overrides the grooves 10.

In the embodiment of FIG. 6, a MEMS acceleration sensor 18 is located in the flexible tab 14 which again may be connected to a microprocessor. The acceleration sensor 18 detects the oscillating movement of the flexible tab 14 during dose dialing. Thus, the amount of dose selected by rotation of the driver 11 may be determined by the microprocessor on the basis of the signal generated by the acceleration sensor 18 in response to the oscillating radial movement of the flexible tabs 14 during dose dialing.

Figure 7:
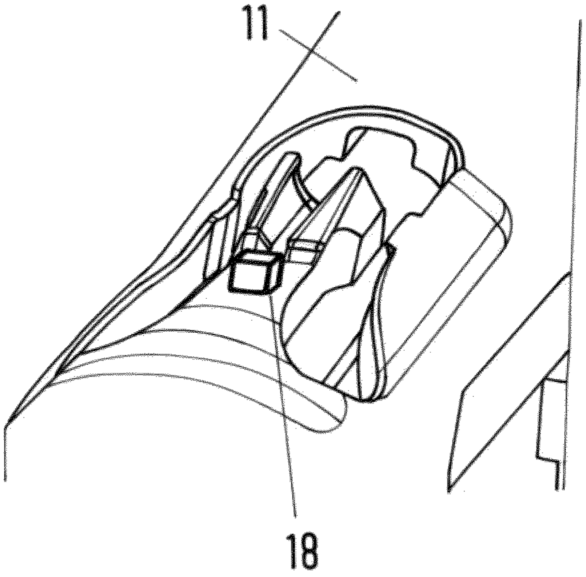
FIG. 7 is a perspective view of the driver of a fifth embodiment.
Figure 8:
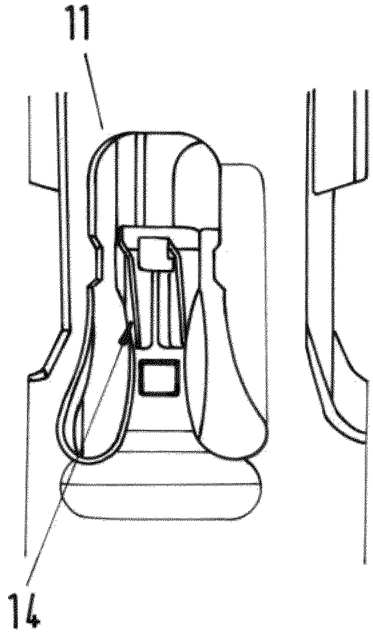
FIG. 8 is a view of the driver of FIG. 7.

A similar embodiment is depicted in FIGS. 7 and 8 showing a driver 11 with a flexible tab 14 on which a MEMS acceleration sensor 18 is located which again may be connected to a microprocessor. The acceleration sensor 18 detects the oscillating movement of the flexible tab 14 during dose dialing.

In further embodiments (not shown), the flexible tab 14 may be made of a light transmitting material. Thus, a light source or an optical sensor may be located remote from the free end of the flexible tab 14. In a similar manner, the clutch sleeve 12 may be made of a light transmitting material, thereby allowing arrangement of a light source or an optical sensor or remote from the aperture 15. Still further, a light source or an optical sensor may be provided on or in the inner housing 9 instead of on or in the clutch sleeve 12.

In other words, according to one aspect of the disclosure, an acceleration MEMS sensor is located on a clicker arm. The clicker arm deflects (clicks) during dialing or dispensing of the device. The sensor measures the acceleration of the arm. The sensor could be either glued on, moulded in or clipped in. As an alternative, an optical sensor is located on the clicker arm or the clicker arm is made of a light transmitting material. The clicker arm deflects sequently during dialing or dispensing of the device. The sensor detects the light coming through or is reflected by the clicker arm in a defined position, at the time the clicker arm is deflect in a second position the sensor is not able to detect the light. Therefore the electronic is able to count units during dialing or dispensing.

REFERENCE NUMERALS

1 drug delivery device
2 cartridge retaining part
3 dose setting and/or drive mechanism
4 number (or dose dialing) sleeve
5 dose dial grip
6 dose display
7 outer housing
8 hub
9 inner housing
10 groove
11 driver
12 clutch sleeve
13 piston rod
14 piston
15 aperture
16 optical sensor (MEMS)
17 light source
18 acceleration sensor (MEMS)

The invention claimed is:

1. A drug delivery device comprising, a dose setting and/or drive mechanism comprising a stationary housing having at least one internal groove on an inner surface;

a driver positioned within the housing which is moveable relative to the housing during dose dialing and which is moveable relative to the housing during dose dispensing;

at least one flexible tab that is biased to engage the at least one internal groove such that the at least one flexible tab repeatedly engages and disengages the at least one internal groove during dose dialing, thereby performing an oscillating movement between two positions comprising a first position in which the at least one flexible tab engages the at least one internal groove and a second position in which the at least one flexible tab is disengaged from the at least one internal groove;

a blocking member slidably positioned inside the driver that locks the at least one flexible tab into the at least one internal groove during dose dispensing such that the driver follows the path of the at least one internal groove; and at least one micro-electro-mechanical system comprising at least one sensor configured and arranged to detect the oscillating movement of the at least one flexible tab during dose dialing.

2. The drug delivery device according to claim 1, wherein the driver is rotatable relative to the housing during dose dialing and is axially displaceable relative to the housing during dose dispensing.

3. The drug delivery device according to claim 1, wherein the at least one sensor is an acceleration sensor located in or on the at least one flexible tab.

4. The drug delivery device according to claim 1, further comprising a light source, wherein the at least one sensor is an optical sensor located in or on the at least one flexible tab and aligned with the light source such that light emitted by the light source can be detected by the sensor only in one of the first or second position, whereas the light emitted by the light source cannot be detected by the sensor in the other of the two positions.

5. The drug delivery device according to claim 1, further comprising a light source located in or on the at least one flexible tab, wherein the at least one sensor is an optical sensor aligned with the light source such that light emitted by the light source can be detected by the sensor only in one of the first or second position, whereas the light emitted by the light source cannot be detected by the sensor in the other of the two positions.

6. The drug delivery device according to claim 1, further comprising a light source, wherein the at least one flexible tab is made of a light transmitting material and the light source is located to introduce light into the at least one flexible tab, wherein the at least one sensor is an optical sensor located aligned with the at least one flexible tab such that light emitted by the at least one flexible tab can be detected by the sensor only in one of the first or second position, whereas the light emitted by the at least one flexible tab cannot be detected by the sensor in the other of the two positions.

7. The drug delivery device according to claim 1, wherein the at least one micro-electro-mechanical system further comprises a microprocessor which is operatively connected to the at least one sensor, to a power source, and to a memory, wherein the microprocessor is configured to determine a dose amount selected by rotation of the driver during dose dialing.

8. The drug delivery device according to claim 7, further comprising a communication unit connected to the at least one micro-electro-mechanical system and configured to transmit data corresponding to the dose amount determined by the microprocessor to a remote data management unit.

9. The drug delivery device according to claim 1, wherein the at least one flexible tab is an integral part of the driver.

10. The drug delivery device according to claim 9, wherein the blocking member has an aperture or pocket that is aligned with the flexible tab when the blocking member is in a non-locked position and is misaligned with the flexible tab when in the locked position.

11. The drug delivery device according to claim 10, wherein the aperture or pocket is aligned with the flexible tab during dose dialing and is misaligned with the flexible tab during dose delivery.

12. The drug delivery device according to claim 1, wherein the blocking member is provided with the at least one flexible tab.

13. The drug delivery device according to claim 12, wherein the driver has an aperture or pocket that is aligned with the flexible tab when the blocking member is in a non-locked position and is misaligned with the flexible tab when in the locked position.

14. The drug delivery device according to claim 13, wherein the aperture or pocket is aligned with the flexible tab during dose dialing and is misaligned with the flexible tab during dose delivery.

15. The drug delivery device according to claim 1, further comprising a cartridge containing a medicament.

16. A method for determining a dialed or dispensed dose in a drug delivery device, the drug delivery device comprising a stationary housing having at least one internal groove on an inner surface; a driver positioned within the housing which is moveable relative to the housing during dose dialing and which is moveable relative to the housing during dose dispensing; at least one flexible tab that is biased to engage the at least one internal groove such that the at least one flexible tab repeatedly engages and disengages the at least one internal groove during dose dialing, thereby performing an oscillating movement between two positions comprising a first position in which the at least one flexible tab engages the at least one internal groove and a second position in which the at least one flexible tab is disengaged from the at least one internal groove; a blocking member slidably positioned inside the driver that locks the at least one flexible tab into the at least one internal groove during dose dispensing such that the driver follows the path of the at least one internal groove; and at least one micro-electro-mechanical system comprising at least one sensor configured and arranged to detect the oscillating movement of the at least one flexible tab during dose dialing, a microprocessor which is operatively connected to the at least one sensor, to a power source, and to a memory, wherein the microprocessor is configured to determine a dose amount selected by rotation of the driver during dose dialing; the method comprising:

dialing a dose by moving the driver; and inducing the at least one sensor of the at least one micro-electro-mechanical system to detect the oscillating movement of the at least one flexible tab and processing a signal generated by the at least one sensor in response to the oscillating movement of the at least one flexible tab in the microprocessor to determine a dose amount selected by movement of the driver during dose dialing.

17. The method according to claim 16, wherein moving the drive comprises rotating the driver.

18. The method according to claim 16, further comprising transmitting data corresponding to the dose amount determined by the microprocessor to a remote data management unit.

19. The method according to claim 16, wherein the at least one sensor comprises an acceleration sensor.

20. The method according to claim 16, wherein the drug delivery device further comprises a light source and the at least one sensor comprises an optical sensor.

* * * * *